United States Patent
Ma

(10) Patent No.: US 9,750,927 B2
(45) Date of Patent: Sep. 5, 2017

(54) BLOOD CONTROL CATHETER WITH ANTIMICROBIAL NEEDLE LUBE

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/341,944

(22) Filed: Nov. 2, 2016

(65) Prior Publication Data

US 2017/0056639 A1     Mar. 2, 2017

Related U.S. Application Data

(63) Continuation-in-part of application No. 15/138,864, filed on Apr. 26, 2016, which is a continuation of (Continued)

(51) Int. Cl.
    *A61M 5/00*     (2006.01)
    *A61M 31/00*    (2006.01)
    (Continued)

(52) U.S. Cl.
    CPC ......... *A61M 39/10* (2013.01); *A61B 17/3421* (2013.01); *A61L 29/14* (2013.01);
    (Continued)

(58) Field of Classification Search
    CPC ........... A61L 2300/404; A61L 2400/10; A61L 29/14; A61L 29/16; A61M 2025/0046;
    (Continued)

(56) References Cited

U.S. PATENT DOCUMENTS 3,223,629 A   12/1965 Loeffler
4,339,336 A    7/1982 Hammond et al.
(Continued)

FOREIGN PATENT DOCUMENTS

CN      1526771 A    9/2004
CN    101353545 A    1/2009
(Continued)

OTHER PUBLICATIONS

McDonnell, G., et al., "Antiseptics and Disinfectants: Activity, Action, and Resistance," Clinical Microbiology Reviews, Jan. 1999, vol. 12, No. 1, pp. 149-179.
(Continued)

*Primary Examiner* — Jason Flick
(74) *Attorney, Agent, or Firm* — Jeanne Lukasavage; Craig Metcalf; Kirton McConkie

(57) ABSTRACT

An antimicrobial lubricant applied to an outer surface of an introducer needle as part of a catheter assembly device. The catheter assembly device further includes a septum having a slit through which the introducer needle is threaded. The antimicrobial lubricant is squeegeed, or removed from the outer surface of the introducer needle as the needle is removed from the slit following catheterization. The removed antimicrobial lubricant forms a deposit on the septum at a location proximate to the slit, thereby preventing colonization and growth of pathogens on the septum and other adjacent components and surfaces of the catheter assembly device.

20 Claims, 11 Drawing Sheets

Related U.S. Application Data application No. 13/793,569, filed on Mar. 11, 2013, now Pat. No. 9,327,095.

(51) Int. Cl.

| | | |
|---|---|---|
| *A61M 39/10* | (2006.01) | |
| *A61M 25/06* | (2006.01) | |
| *A61L 29/16* | (2006.01) | |
| *A61L 29/14* | (2006.01) | |
| *A61B 17/34* | (2006.01) | |
| *A61M 25/00* | (2006.01) | |
| *A61M 39/06* | (2006.01) | |
| *A61M 39/16* | (2006.01) | |
| *A61M 39/00* | (2006.01) | |
| *A61B 17/00* | (2006.01) | |

(52) U.S. Cl.
CPC ........... *A61L 29/16* (2013.01); *A61M 25/002* (2013.01); *A61M 25/0043* (2013.01); *A61M 25/065* (2013.01); *A61M 25/0606* (2013.01); *A61M 39/0606* (2013.01); *A61M 39/16* (2013.01); *A61M 39/162* (2013.01); *A61B 2017/00889* (2013.01); *A61L 2300/404* (2013.01); *A61L 2400/10* (2013.01); *A61L 2420/02* (2013.01); *A61M 25/0045* (2013.01); *A61M 25/0097* (2013.01); *A61M 2025/0019* (2013.01); *A61M 2025/0046* (2013.01); *A61M 2025/0056* (2013.01); *A61M 2025/0062* (2013.01); *A61M 2039/0036* (2013.01); *A61M 2039/062* (2013.01); *A61M 2039/064* (2013.01); *A61M 2039/068* (2013.01); *A61M 2039/1077* (2013.01); *A61M 2205/0205* (2013.01); *A61M 2205/0222* (2013.01)

(58) Field of Classification Search
CPC .. A61M 2025/0056; A61M 2039/0036; A61M 2039/062; A61M 2039/064; A61M 2039/068; A61M 2205/0205; A61M 2205/0222; A61M 25/002; A61M 25/0043; A61M 25/0045; A61M 25/0097; A61M 25/0606; A61M 39/0606; A61M 39/162
USPC ........................................................ 604/500
See application file for complete search history.

(56) References Cited

U.S. PATENT DOCUMENTS

| | | | |
|---|---|---|---|
| 4,584,192 A | 4/1986 | Dell et al. | |
| 4,603,152 A | 7/1986 | Laurin et al. | |
| 4,629,743 A | 12/1986 | Hong | |
| 4,629,746 A | 12/1986 | Michl et al. | |
| 4,642,126 A | 2/1987 | Zador et al. | |
| 4,676,782 A | 6/1987 | Yamamoto et al. | |
| 4,677,143 A | 6/1987 | Laurin et al. | |
| 4,716,032 A | 12/1987 | Westfall et al. | |
| 4,798,594 A | 1/1989 | Hillstead | |
| 4,895,566 A | 1/1990 | Lee | |
| 4,915,934 A | 4/1990 | Tomlinson | |
| 4,925,668 A * | 5/1990 | Khan | A61L 29/06 264/209.1 |
| 4,955,890 A | 9/1990 | Yamamoto et al. | |
| 4,985,399 A | 1/1991 | Matsuda et al. | |
| 5,023,082 A | 6/1991 | Friedman et al. | |
| 5,217,493 A | 6/1993 | Raad et al. | |
| 5,366,505 A | 11/1994 | Farber | |
| 5,456,948 A | 10/1995 | Mathisen et al. | |
| 5,512,199 A | 4/1996 | Khan et al. | |
| 5,540,661 A | 7/1996 | Tomisaka et al. | |
| 5,547,662 A | 8/1996 | Khan et al. | |
| 5,616,338 A | 4/1997 | Fox, Jr. et al. | |
| 5,638,812 A | 6/1997 | Turner | |
| 5,653,695 A | 8/1997 | Hopkins et al. | |
| 5,698,229 A | 12/1997 | Ohsumi et al. | |
| 5,712,229 A | 1/1998 | Hopkins et al. | |
| 5,716,406 A | 2/1998 | Farber | |
| 5,763,412 A | 6/1998 | Khan et al. | |
| 5,773,487 A | 6/1998 | Sokol | |
| 5,861,440 A | 1/1999 | Goh la et al. | |
| 6,051,609 A | 4/2000 | Yu et al. | |
| 6,120,784 A | 9/2000 | Snyder, Jr. | |
| 6,127,320 A | 10/2000 | van Ooij et al. | |
| 6,242,526 B1 | 6/2001 | Siddiqui et al. | |
| 6,248,811 B1 | 6/2001 | Ottersbach et al. | |
| 6,326,417 B1 | 12/2001 | Jia | |
| 6,337,357 B1 | 1/2002 | Fukunishi et al. | |
| 6,353,041 B1 | 3/2002 | Qian | |
| 6,413,539 B1 | 7/2002 | Shalaby | |
| 6,475,434 B1 | 11/2002 | Darouiche | |
| 6,488,942 B1 | 12/2002 | Ingemann | |
| 6,492,445 B2 | 12/2002 | Siddiqui et al. | |
| 6,576,633 B1 | 6/2003 | Young et al. | |
| 6,579,539 B2 | 6/2003 | Lawson et al. | |
| 6,719,991 B2 | 4/2004 | Darouiche et al. | |
| 6,723,350 B2 | 4/2004 | Burrell et al. | |
| 6,843,784 B2 | 1/2005 | Modak et al. | |
| 6,846,846 B2 | 1/2005 | Modak et al. | |
| 6,861,060 B1 | 3/2005 | Luriya et al. | |
| 6,887,270 B2 | 5/2005 | Miller et al. | |
| 6,896,889 B2 | 5/2005 | Chevalier et al. | |
| 7,074,839 B2 | 7/2006 | Fansler et al. | |
| 7,098,256 B2 | 8/2006 | Ong et al. | |
| 7,179,849 B2 | 2/2007 | Terry | |
| 7,198,800 B1 | 4/2007 | Ko | |
| 7,232,540 B2 | 6/2007 | Gould et al. | |
| 7,261,925 B2 | 8/2007 | Nesbitt | |
| 7,268,165 B2 | 9/2007 | Greten et al. | |
| 7,407,707 B2 | 8/2008 | Gould et al. | |
| 7,462,401 B2 | 12/2008 | Halfyard et al. | |
| 7,494,339 B2 | 2/2009 | Dias et al. | |
| 7,498,367 B2 | 3/2009 | Qian | |
| 7,514,477 B2 | 4/2009 | Klare et al. | |
| 7,816,434 B2 | 10/2010 | Hackbarth et al. | |
| 8,034,455 B2 | 10/2011 | Wang et al. | |
| 8,227,050 B1 | 7/2012 | O'Neil | |
| 8,263,102 B2 | 9/2012 | Labrecque et al. | |
| 8,388,583 B2 | 3/2013 | Stout et al. | |
| 8,414,547 B2 | 4/2013 | Di Fiore et al. | |
| 9,327,095 B2 | 5/2016 | Ma | |
| 2001/0010016 A1 | 7/2001 | Modak et al. | |
| 2001/0016589 A1 | 8/2001 | Modak et al. | |
| 2001/0056133 A1 | 12/2001 | Montgomery et al. | |
| 2002/0009436 A1 | 1/2002 | Doyle et al. | |
| 2002/0028751 A1 | 3/2002 | Lokkesmoe et al. | |
| 2002/0037260 A1 | 3/2002 | Budny et al. | |
| 2002/0040092 A1 | 4/2002 | Siddiqui et al. | |
| 2002/0064858 A1 | 5/2002 | Yacoby-Zeevi | |
| 2002/0091424 A1 | 7/2002 | Biel | |
| 2002/0119111 A1 | 8/2002 | Kilgour et al. | |
| 2002/0133124 A1 | 9/2002 | Leinsing et al. | |
| 2002/0144705 A1 | 10/2002 | Brattesani et al. | |
| 2003/0072781 A1 | 4/2003 | Pelerin | |
| 2003/0105143 A1 | 6/2003 | Ammendola et al. | |
| 2003/0119932 A1 | 6/2003 | Al-Akhdar et al. | |
| 2003/0134783 A1 | 7/2003 | Harshey et al. | |
| 2003/0144362 A1 | 7/2003 | Utterberg et al. | |
| 2003/0147932 A1 | 8/2003 | Nun et al. | |
| 2003/0162839 A1 | 8/2003 | Symington et al. | |
| 2003/0170308 A1 | 9/2003 | Cleary et al. | |
| 2003/0176848 A1 | 9/2003 | Gibson et al. | |
| 2003/0206875 A1 | 11/2003 | Budny et al. | |
| 2003/0215433 A1 | 11/2003 | Kokai-Kun et al. | |
| 2003/0224032 A1 | 12/2003 | Read et al. | |
| 2004/0039349 A1 | 2/2004 | Modak et al. | |
| 2004/0058829 A1 | 3/2004 | Hei et al. | |
| 2004/0109852 A1 | 6/2004 | Xu | |
| 2004/0115477 A1 | 6/2004 | Nesbitt | |
| 2004/0132164 A1 | 7/2004 | Doyle et al. | |
| 2004/0180829 A1 | 9/2004 | Bassler et al. | |

(56) References Cited

U.S. PATENT DOCUMENTS

| | | |
|---|---|---|
| 2004/0185296 A1 | 9/2004 | Mazzanti |
| 2004/0230162 A1 | 11/2004 | Tan |
| 2004/0234475 A1 | 11/2004 | Lannibois-Drean et al. |
| 2005/0008671 A1 | 1/2005 | Van Antwerp |
| 2005/0048005 A1 | 3/2005 | Stockel |
| 2005/0048124 A1 | 3/2005 | Sarangapani |
| 2005/0059731 A1 | 3/2005 | Albrecht et al. |
| 2005/0100580 A1 | 5/2005 | Osborne et al. |
| 2005/0118239 A1 | 6/2005 | Sabesan |
| 2005/0131356 A1 | 6/2005 | Ash et al. |
| 2005/0143286 A1 | 6/2005 | Singh et al. |
| 2005/0158253 A1 | 7/2005 | Budny et al. |
| 2005/0176905 A1 | 8/2005 | Moon et al. |
| 2005/0233950 A1 | 10/2005 | Madhyastha |
| 2005/0265931 A1 | 12/2005 | Qian |
| 2006/0024372 A1 | 2/2006 | Utterberg et al. |
| 2006/0165751 A1 | 7/2006 | Chudzik et al. |
| 2006/0165903 A1 | 7/2006 | Mazzanti |
| 2006/0239954 A1 | 10/2006 | Sancho |
| 2006/0258780 A1 | 11/2006 | Chaussade et al. |
| 2007/0000407 A1 | 1/2007 | Leong |
| 2007/0112112 A1 | 5/2007 | Kerschner et al. |
| 2007/0112146 A1 | 5/2007 | Falk et al. |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0275101 A1 | 11/2007 | Lu et al. |
| 2008/0026026 A1 | 1/2008 | Lu et al. |
| 2008/0051737 A1 | 2/2008 | Paul et al. |
| 2008/0075761 A1 | 3/2008 | Modak et al. |
| 2008/0161763 A1 | 7/2008 | Harding et al. |
| 2008/0182921 A1 | 7/2008 | Suh et al. |
| 2009/0012220 A1 | 1/2009 | Yamane et al. |
| 2009/0101152 A1 | 4/2009 | Burk et al. |
| 2009/0110844 A1 | 4/2009 | Platzer et al. |
| 2009/0114327 A1 | 5/2009 | Breunig |
| 2009/0162530 A1 | 6/2009 | Nesbitt |
| 2009/0176907 A1 | 7/2009 | Subramanian et al. |
| 2009/0188559 A1 | 7/2009 | Nesbitt |
| 2009/0220739 A1 | 9/2009 | Chougule |
| 2010/0135949 A1 | 6/2010 | Ou-Yang |
| 2010/0136209 A1 | 6/2010 | Ou-Yang et al. |
| 2010/0137379 A1 | 6/2010 | Ou-Yang |
| 2010/0137472 A1 | 6/2010 | Ou-Yang |
| 2010/0204648 A1* | 8/2010 | Stout .............. A61M 25/0606 604/122 |
| 2011/0009831 A1 | 1/2011 | Burkholz et al. |
| 2011/0065798 A1 | 3/2011 | Hoang et al. |
| 2011/0301553 A1* | 12/2011 | Goral .............. A01N 25/04 604/265 |
| 2013/0090610 A1* | 4/2013 | Stout .............. A61M 25/0097 604/256 |
| 2013/0261722 A1* | 10/2013 | Hossainy .............. A61F 2/00 623/1.11 |

FOREIGN PATENT DOCUMENTS

| | | |
|---|---|---|
| CN | 102355923 | 2/2012 |
| DE | 4011867 A1 | 10/1991 |
| EP | 0 036 294 A2 | 9/1981 |
| EP | 0 338 418 A1 | 10/1989 |
| EP | 0 379 271 A2 | 7/1990 |
| EP | 0 396 431 A1 | 11/1990 |
| JP | 05-277434 A | 10/1993 |
| JP | 09-151262 A | 6/1997 |
| JP | H09176677 | 7/1997 |
| JP | H10231 | 1/1998 |
| JP | 2002-282762 A | 10/2002 |
| JP | 2003-342402 A | 12/2003 |
| JP | 2005515838 | 6/2005 |
| JP | 2008533051 | 8/2008 |
| JP | 2012532681 | 12/2012 |
| KR | 2002-0066429 A | 8/2002 |
| WO | 98/58690 A2 | 12/1998 |
| WO | 98/58989 A1 | 12/1998 |
| WO | 99/32168 A1 | 7/1999 |
| WO | 00/66189 A2 | 11/2000 |
| WO | 2004/108091 A2 | 12/2004 |
| WO | 2006/056482 A1 | 6/2006 |
| WO | 2006/074666 A2 | 7/2006 |
| WO | 2006/099358 A2 | 9/2006 |
| WO | 2007/064835 A2 | 6/2007 |
| WO | 2007/100653 A2 | 9/2007 |
| WO | 2007/100776 A2 | 9/2007 |
| WO | 2008/014447 A2 | 1/2008 |
| WO | 2008/013601 A1 | 3/2008 |
| WO | 2008/031601 A1 | 3/2008 |
| WO | 2008/132045 A2 | 11/2008 |
| WO | 2014/143600 | 9/2014 |

OTHER PUBLICATIONS

"Address Multi-Drug Resistant Organisms on the Skin with Early Preop Prep," Sage Products, Inc., Retrieved from the Internet URL: http://www.sageproducts.com/products/ssi-prevention.cfm, on Oct. 31, 2008, p. 1.

"ChloraPrep," Enturia, Retrieved from the internet URL: http://www.enturia.com/products/chloraPrep/chloraPrep-product.html, on Oct. 31, 2008, p. 1-3.

"Clinell Alcoholic 2% Chlorhexidine," Gama Healthcare, Retrieved from the internet URL: http://www.gamahealthcare.com/clinellaca2c.html, on Nov. 7, 2008, p. 1-3.

"ComfortCoat Hydrophilic Coating," DSM in Medical, Retrieved from the internet URL: http://www.dsm.com/en_US/medical/public/home/pages/product-coating-comfortcoat.jsp, updated Jan. 11, 2013, on Apr. 22, 2013.

"Lubricent-Lubricious Hydrophillic Coatings for Medical Devices," Harland Medical Systems, Retrieved from the Internet URL: http://www.harlandmedical.com/index.php/materials/lubricent.html, on Apr. 22, 2013, p. 1-2.

"Preoperative Skin Preparation and Peri operative Oral Care for the Short-Term Ventilated Patient," Sage Products, Inc., Retrieved from the internet URL: http://www.sageproducts.com/products/ssi-vap-prevention.cfm, on Oct. 31, 2008, p. 1.

"Preoperative Skin Preparation for the Surgical Patient," Sage Products, Inc., Retrieved from the internet URL: http://www.sageproducts.com/products/skin-prep.cfm, on Oct. 31, 2008, p. 1.

"Using Silicas and Aluminas in Coatings," Retrieved from the internet URL: www.cabot-corp.com/Silicas-And-Aluminas/Coatings, on Apr. 26, 2011.

"UV & EB Cure," Xiper Innovations, Inc., Retrieved from the internet URL: http://xiperinnovations.com/uv-eb-cure, on Mar. 16, 2017.

* cited by examiner

BLOOD CONTROL CATHETER WITH ANTIMICROBIAL NEEDLE LUBE

RELATED APPLICATIONS

This application is a continuation-in-part of U.S. patent application Ser. No. 15/138,864, filed Apr. 26, 2016, entitled BLOOD CONTROL CATHETER WITH ANTIMICROBIAL NEEDLE LUBE, which is a continuation of U.S. patent application Ser. No. 13/793,569, filed Mar. 11, 2013, entitled BLOOD CONTROL CATHETER WITH ANTIMICROBIAL NEEDLE LUBE, and now issued as U.S. Pat. No. 9,327,095, which are incorporated herein in their entirety.

BACKGROUND OF THE INVENTION

The current invention relates to a lubricant for dermally invasive devices. In particular, the present invention relates to methods and systems whereby an antimicrobial lubricant is applied to the outer surface of a catheter device to prevent infection.

Catheters are commonly used for a variety of infusion therapies. For example, catheters are used for infusing fluids, such as normal saline solution, various medicaments, and total parenteral nutrition into a patient, withdrawing blood from a patient, as well as monitoring various parameters of the patient's vascular system.

Catheters are commonly introduced into the vasculature of a patient as part of an intravenous catheter assembly. The catheter assembly generally includes a catheter adapter, which supports the catheter, the catheter adapter being coupled to a needle hub which supports an introducer needle. The introducer needle is extended and positioned within the catheter such that a beveled portion of the needle is exposed beyond a tip of the catheter. The beveled portion of the needle is used to pierce the skin of the patient to provide an opening whereby to insert the needle in the vasculature of the patient. Following insertion and placement of the catheter, the introducer needle is removed from the catheter thereby providing intravenous access to the patient.

Catheter-related bloodstream infections are caused by the colonization of microorganisms in patients with intravascular catheters and I.V. access devices. These infections are an important cause of illness and excess medical costs, as approximately 250,000 catheter-related bloodstream infections occur in United States intensive care units each year. In addition to the monetary costs, these infections are associated with anywhere from 20,000 to 100,000 deaths each year.

Despite guidelines to help reduce healthcare associated infections (HAIs), catheter-related bloodstream infections continue to plague our healthcare system. The 10 most common pathogens (accounting for 84% of any HAIs) were coagulase-negative staphylococci (15%), *Staphylococcus aureus* (15%), *Enterococcus* species 12%), *Candida* species (11%), *Escherichia coli* (10%), *Pseudomonas aeruginosa* (8%), *Klebsiella pneumoniae* (6%), *Enterobacter* species (5%), *Acinetobacter baumannii* (3%), and *Klebsiella oxytoca* (2%). The pooled mean proportion of pathogenic isolates resistant to antimicrobial agents varied significantly across types of HAI for some pathogen-antimicrobial combinations. As many as 16% of all HAIs were associated with the following multidrug-resistant pathogens: methicillin-resistant *S. aureus* (8% of HAIs), vancomycin-resistant *Enterococcus faecium* (4%), carbapenem-resistant *P. aerugi-nosa* (2%), extended-spectrum cephalosporin-resistant *K. pneumoniae* (1%), extended-spectrumcephalosporin-resistant *E. coli* (0.5%), and carbanpenem-resistant *A. baumannii, K. pneumoniae, K. oxytoca,* and *E. coli* (0.5%) antimicrobial-resistant pathogens.

Impregnating catheters with various antimicrobial agents is one approach that has been implemented to prevent these infections. These catheters, however, have given less than satisfactory results. For example, these catheters are largely ineffective at preventing growth and colonization of pathogens on interior surfaces and components of a catheter assembly. In addition, some microbes have developed resistance to the various antimicrobial agents in the system.

Accordingly, there is a need in the art for dermally invasive devices having improved antimicrobial capabilities. Such methods and systems are disclosed herein.

BRIEF SUMMARY OF THE INVENTION

In order to overcome the limitations discussed above, the present invention relates to an antimicrobial lubricant matrix applied to a catheter device such that upon fully inserting the catheter device into a patient, the antimicrobial lubricant is interposed between the catheter and the dermal layers of the patient.

In some implementations, an antimicrobial formulation is provided as an insoluble lubricant material that is applied to an outer surface of an introducer needle as part of an intravenous catheter assembly. The lubricant material is applied so that as the needle is withdrawn through a blood control septum of the catheter assembly, a slit of the septum "squeegees" or otherwise removes a portion of the lubricant material from the outer surface of the needle. The removed lubricant material collects on the membrane and slit of the septum to provide a physical barrier between the slit and the vasculature of the patient. In some instances, a portion of the removed lubricant material is deposited within the slit, thereby further closing or sealing the slit.

In some instances, the lubricant material further comprises a lubricious agent. The lubricious agent reduces friction between the slit and the outer surface of the needle. As such, the needle may be removed through the septum in smooth and continuous manner without catching or otherwise damaging the septum's slit. The lubricious agent of the lubricant material may further reduce friction between the septum and an external Luer device that is inserted through the slit. The antimicrobial lubricant may be transferred to the Luer device as it is inserted through the slit, thereby killing any pathogens present thereon. In some implementations, the antimicrobial lubricant further includes an anti-thrombogenic agent to decrease the likelihood of blood clots within the catheter assembly.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
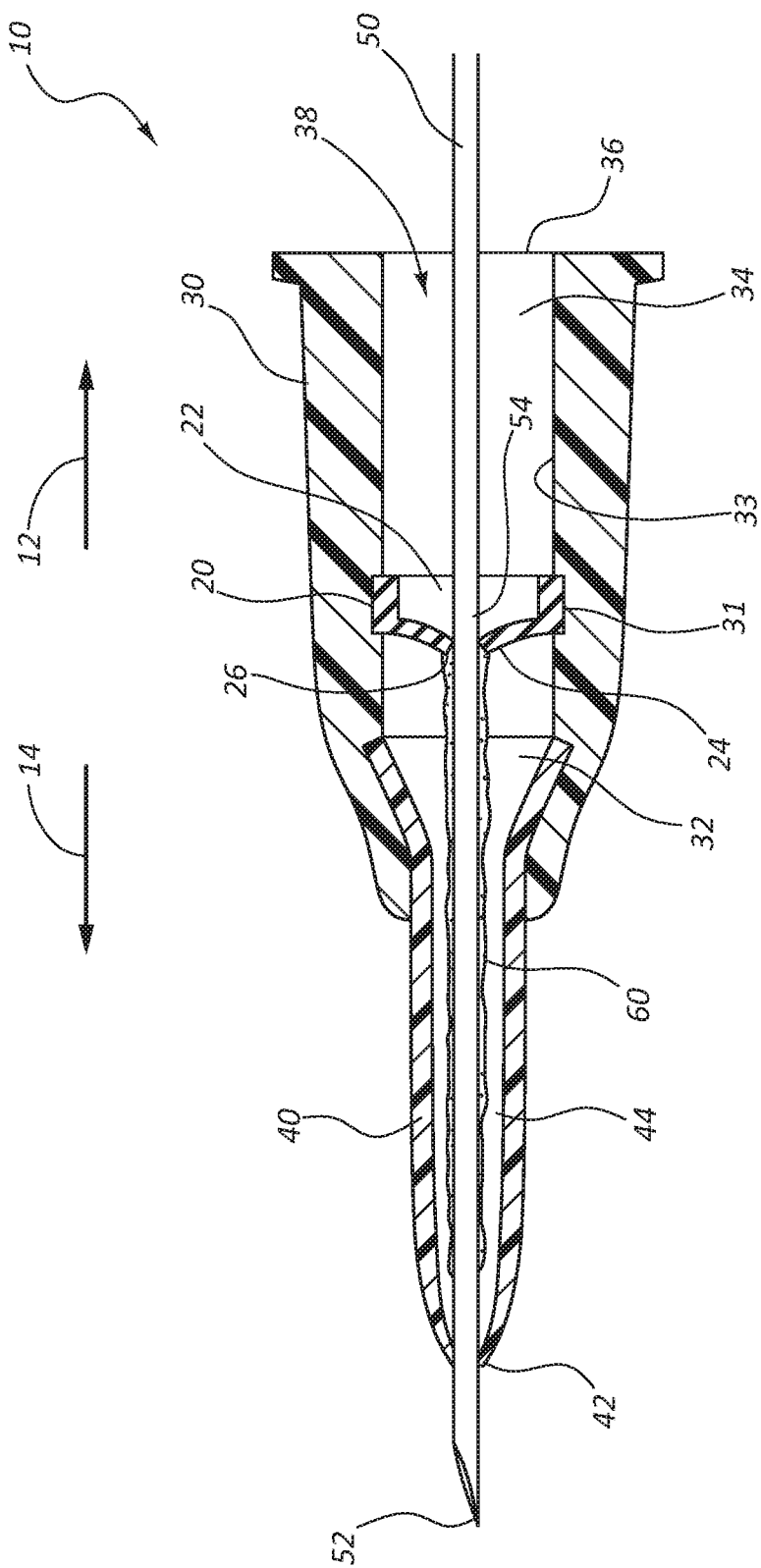
FIG. 1 is a cross-section view of a catheter assembly having a coated introducer needle positioned prior to being withdrawn from the catheter adapter in accordance with a representative embodiment of the present invention.

Referring now to FIG. 1, a catheter device assembly 10 is shown. In general, a catheter device assembly 10 in accordance with the present invention provides access to the vasculature of a patient, such as for infusion therapy procedures or blood collection. In some embodiments, catheter device system 10 comprises a catheter adapter 30 which supports a catheter tube 40. Catheter tube 40 extends outwardly from catheter adapter 30 and is in fluid communication therewith.

In some embodiments, catheter device system 10 further comprises a needle hub (not shown) which supports an introducer needle 50. Introducer needle 50 is threadedly positioned through catheter adapter 30 and catheter tube 40 such that a beveled tip 52 of needle 50 extends beyond catheter tip 42. Beveled tip 52 provides a cutting surface whereby to penetrate the patient's skin and provide access to the patient's vasculature. Once catheter 40 is fully inserted into the patient, introducer needle 50 is removed thereby providing intravenous access to the patient 20 via catheter 40 and catheter adapter 30.

In some embodiments, catheter adapter 30 further comprises a blood control septum 20. Blood control septum 20 is provided as a physical barrier to control the flow of blood and other fluids between the forward chamber 32 and the rearward chamber 34 of catheter adapter 30. For example, upon insertion of beveled tip 52 and catheter tip 42 into the patient's vein and the removal of the needle 50, blood from the patient flows through lumen 44 of catheter tube 40 and into forward chamber 32. The patient's blood is prevented from bypassing septum 20, thereby retaining the blood in forward chamber 32. Without blood control septum 20 in place, blood would flow into rearward chamber 34 and out of opening 36 in an uncontrolled manner. This would result in undesirable exposure of the user to the patient's blood. Accordingly, blood control septum 20 is positioned in fluid pathway 38 of catheter adapter 30 to prevent the user from being exposed to the patient's blood.

In some instances, blood control septum 20 is seated into an annular groove 31 that is provided in the inner surface 33 of catheter adapter 30. In some embodiments, blood control septum 20 comprises an outer diameter that is greater than an inner diameter of fluid pathway 38, and is slightly larger than the diameter of annular groove 31. Thus, blood control septum 20 is seated into annular groove 31 and is prevented from moving within fluid pathway 38 in proximal 12 and distal 14 directions. In other instances, the outer peripheral edge of blood control septum 20 is secured to inner surface 33 via an adhesive, plastic weld, or other mechanical connection (such as a retainer clip).

Blood control septum 20 may comprise any structural configuration which is capable of dividing fluid pathway 38 into forward and rearward chambers 32 and 34. For example, in some embodiments blood control septum 20 comprises a disc. In other embodiments, blood control septum 20 comprises a cylinder having a proximal opening 22 and a distal cap forming a membrane 24. In some embodiments, membrane 24 comprises a slit 26 or a plurality of slits which form a pathway through membrane 24. Slit 26 may be configured to permit passage of introducer needle 50 through septum 20.

The resilient or stretchy nature of septum 20 permits slits 26 to stretch and thereby accommodate passage of needle 50. In some instances, a seal or interface between slit 26 and the outer surface of needle 50 is sufficiently tight so that slit 26 prevents passage of fluid from forward chamber 32 to rearward chamber 34 when needle 50 is moved in proximal direction 12. Further, blood that is present on outer surface 54 of the portion of needle 50 located in forward chamber 32 is removed or "squeegeed" from outer surface 54 as needle 50 moved through slit 26 in proximal direction 12. Upon complete removal of needle 50 from slit 26, slit 26 self-closes, thereby further preventing fluid within forward chamber 32 from passing into rearward chamber 34.

Typically, the introducer needle 50 is coated with an oily lubricant that helps to reduce the system drag during needle removal. In some embodiments, the lubricant further comprises an antimicrobial agent forming an antimicrobial lubricant 60. The antimicrobial lubricant 60 is provided as a means for preventing colonization and growth of microbes and pathogens within catheter assembly 10. In some embodiments the antimicrobial lubricant 60 is applied to entire outer surface 54 of needle 50. In some instances, the antimicrobial lubricant 60 is applied to the portion of outer surface 54 that is located in forward chamber 32. During clinical usage, as the introducer needle is removed from the catheter, part of the antimicrobial lubricant 60 is removed or "squeegeed" from outer surface 54 as needle 50 moved through slit 26 in proximal direction 12, forming an antimicrobial barrier on the septum surface and within the slit 26. In this way, antimicrobial lubricant 60 acts as a barrier to prevent bacterial contamination of fluids the catheter.

In some embodiments, an antimicrobial lubricant is insoluable in most infusates and blood thus stay on the septum surfaces during multiple procedures, such as blood drawings, drug infusion, TPN procedures, as well as saline and heparin flushes. Therefore the antimicrobial lubricant can provide long lasting antimicrobial protection.

The formulations of the lubricant in this invention are comprised of a mixture or combination of one or more lubricants, and antimicrobial agents. In the mixture, the antimicrobial agents are uniformly and permanently distributed throughout the lubricant matrix.

In some embodiments, antimicrobial lubricant 60 comprises at least one of a water soluble lubricant, an insoluble lubricant, a viscous gel lubricant, a solid lubricant and a shapeable lubricant.

In some embodiments, antimicrobial lubricant 60 comprises oil lubricant. The oil lubricant can be polydimethyl siloxane, polytrifluoropropylmethyl siloxane, or a copolymer of dimethylsiloxane and trifluoropropylmethylsiloxane. The viscosity of the oil lubricant can be from 20 cp to 1,000,000 cp. In some embodiments, a solvent is added to the oil lubricant with very high viscosity to facilitate application of the antimicrobial lubricant.

Antimicrobial lubricant 60 may be applied to outer surface 54 by dipping, brushing, spraying, or any other compatible techniques known in the art. In some embodiments, excess antimicrobial lubricant 60 is applied to outer surface 54 prior to assembling needle 50 into catheter assembly 10. Needle 50 is inserted through septum 20 and into catheter 40 by providing an enlarged pathway through septum 20. In this way, antimicrobial lubricant 60 is not displaced from outer surface 54 during assembly.

Figure 7:
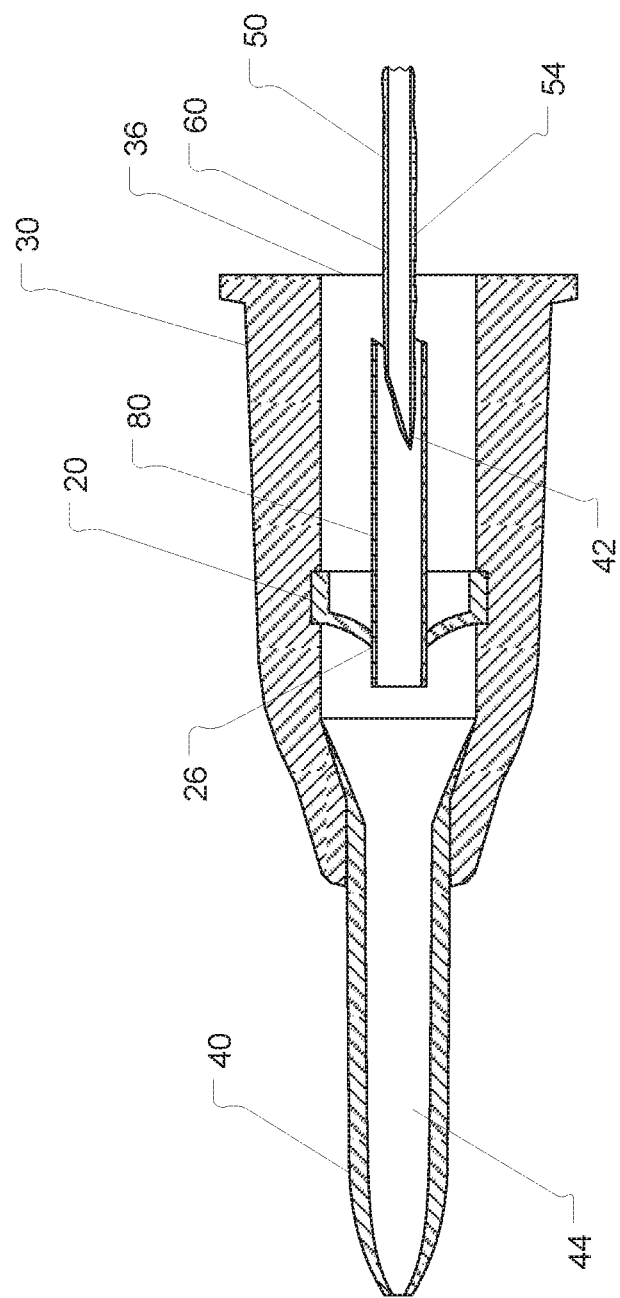
FIG. 7 is a cross-section view of a catheter assembly having a blood control septum with a threader to bias a slit in the septum into an enlarged, opened position in accordance with a representative embodiment of the present invention.

For example, in some embodiments as shown in FIG. 7, a threader 80 is inserted into opening 36 and through slit 26 of septum to bias slit 26 into an enlarged, opened position. The enlarged, opened position of slit 26 is generally greater than the diameter of the coated portion of introducer needle 50. The coated portion of introducer needle 50 is threaded through slit 26 via threader 80, and advanced through lumen 44 of catheter 40 until beveled tip 52 extends beyond catheter tip 42. Once in position, threader 80 is removed from slit 26 and catheter adapter 30. The resilient nature of septum 20 allows slit 26 to resume its closed position around outer surface 54.

Antimicrobial lubricant 60 generally comprises an antimicrobial or biocidal agent effective against various forms and strains of bacteria which may cause infection within a patient. The terms "biocidal agent" or "biocide," as used herein refer to an agent that destroys, inhibits and/or prevents the propagation, growth, colonization and multiplication of unwanted organisms. The term "organism" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria. Specific examples of such organisms include the fungi *Aspergillus niger, Aspergillus flavus, Rhizopus nigricans, Cladosprorium herbarium, Epidermophyton floccosum, Trichophyton mentagrophytes, Histoplasma capsulatum*, and the like; bacteria such as *Pseudomanas aeruginosa, Escherichia coli, Proteus vulgaris, Staphylococcus aureus, Staphylococcus epidermis, Streptococcus faecalis, Klebsiella, Enterobacter aerogenes, Proteus mirabilis*, other gram-negative bacteria and other gram-positive bacteria, mycobactin and the like; and yeast such as *Saccharomcyces cerevisiae, Candida albicans*, and the like. Additionally, spores of microorganisms, viruses and the like are organisms within the scope of the present invention.

Antimicrobial or biocide agents suitable for use in the present invention include, but are not limited to phenol, quaternary ammonium, guanidine, taurolidine, parachlorometaxylenol, silver sulfadiazine, silver oxide, silver nitrate, pyridinium, benzalkonium chloride, cetrimide, benethonium chloride, cetylpyridinium chloride, dequalinium acetate, dequalinium chloride, and chloroxylenol. Further, in some embodiments lubricant 60 comprises a microbial agent selected from chlorhexidine base, chlorhexidine gluconate, chlorhexidine acetate, chlorhexidine hydrochloride, chlorhexidine dihydrochloride, dibromopropamidine, halogenated diphenylalkanes, carbanilide, salicylanilide, tetrachlorosalicylanilide, trichlorocarbanilide, and mixtures thereof. Still further, in some embodiments lubricant 60 comprises a microbial agent selected from chlorhexidine dihydrochloride, chlorhexidine gluconate, chlorhexidine acetate, chlorhexidine diacetate, triclosan, chloroxylenol, dequalinium chloride, benzethonium chloride, benzalkonium chloride, and combinations thereof. The antimicrobial agent can be solid particles that are insoluable in the lubricant or in liquid form. The antimicrobial agent is well mixed within the lubricant prior to application to introducer needles.

In some embodiments, lubricant 60 comprises one or more antimicrobial agents in an amount from approximately 0.01% (w/v) to approximately 10.0% (w/v) of lubricant 60. In other embodiments, lubricant 60 comprises one or more antimicrobial agents in an amount from approximately 0.001% (w/v) to approximately 5.0% (w/v) of lubricant 70. Further, in some embodiments lubricant 60 comprises one or more antimicrobial agents in an amount from approximately 0.01% to approximately 10.0% (w/v).

In some embodiments, lubricant 60 further comprises one or more fugitive solvents, such as tetrahydrofuran (THF), methylethylketone (MEK) and hexane solvents. In some embodiments, lubricant 60 comprises a fugitive solvent in an amount approximately equal to 70% (w/v) of lubricant 60. In other embodiments, lubricant 60 comprises two or more fugitive solvents.

In other embodiments, lubricant 60 comprises one or more alcohol components. Suitable alcohol components generally include a lower alcohol having between one and six carbons ($C_1$-$C_6$). In some embodiments, lubricant 60 comprises an alcohol component selected from the group consisting of ethyl alcohol, isopropanol, propanol, and butanol. In other embodiments, lubricant 60 comprises two or more lower alcohol components, for example a mixture of isopropyl alcohol and ethyl alcohol in a ratio of about 1:10 to about 1:1. Further, in some embodiments lubricant 70 comprises a mixture of more than two alcohol components.

In some embodiments, lubricant 60 comprises an alcohol component in an amount approximately equal to 40% (w/v) of lubricant 60. In other embodiments, lubricant 60 comprises an alcohol component in an amount from approximately 20% (w/v) to approximately 95% (w/v).

In some embodiments, antimicrobial lubricant 60 further comprises a lubricant, such as silicon oil. In some embodiments, introducer needle 50 is coated with a high viscosity antimicrobial lubricant 60 to reduce adhesion between the needle 50 and the catheter tip 42, as well as between the needle 50 and the septum 20. Upon withdrawing needle 50 from catheter 40 and septum 20, slit 26 of septum 20 rubs against the outer surface 54 of the needle 50, thereby removing excess lubricant 60, as shown in FIG. 2.

In some embodiments, antimicrobial lubricant 60 further comprises an anti-thrombogenic agent. An anti-thrombogenic agent is provided to decrease the likelihood of blood clotting within catheter assembly 10. In some instances, an anti-thrombogenic agent is provided to decrease the likelihood of blood clotting within forward chamber 32 or on any surface coated by antimicrobial lubricant 60.

Figure 2:
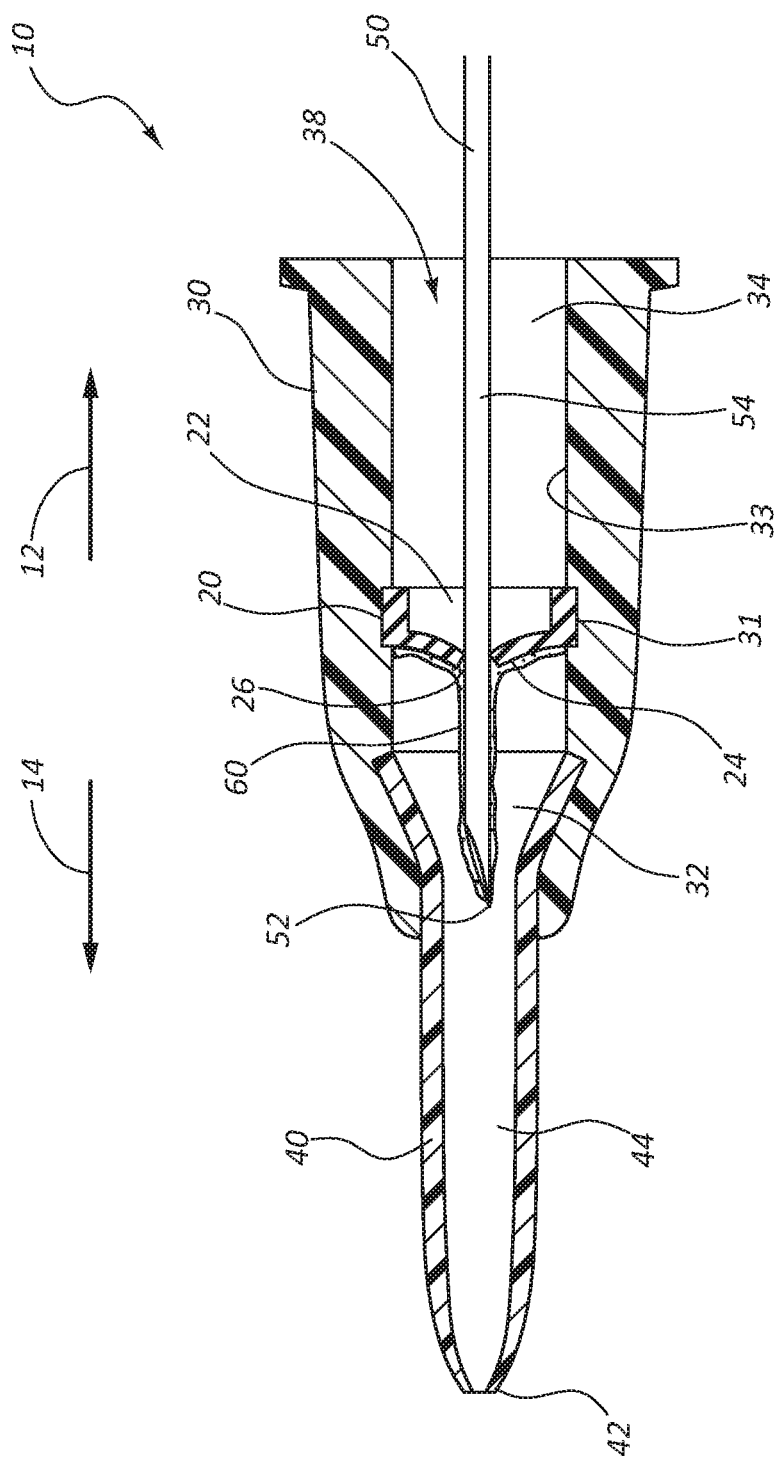
FIG. 2 is a cross-section view of a catheter assembly having a coated introducer needle partially withdrawn from the catheter, wherein an antimicrobial lubricant on the introducer needle has been partially removed from the introducer needle by the blood control septum in accordance with a representative embodiment of the present invention.

Referring now to FIG. 2, catheter assembly 10 is shown having introducer needle 50 partially withdrawn. In some embodiments, excess antimicrobial lubricant 60 is "squeegeed" or removed from outer surface 54 as needle 50 is withdrawn through slit 26 of septum 20 in proximal direction 12. Excess lubricant 60 collects within forward chamber 32 thereby providing a barrier between membrane 24 and forward chamber 32. This barrier will kill microorganisms that come in contact with and/or in close proximity of lubricant preventing microbial growth and colonization on membrane 24 and generally within forward chamber 32.

Figure 3:
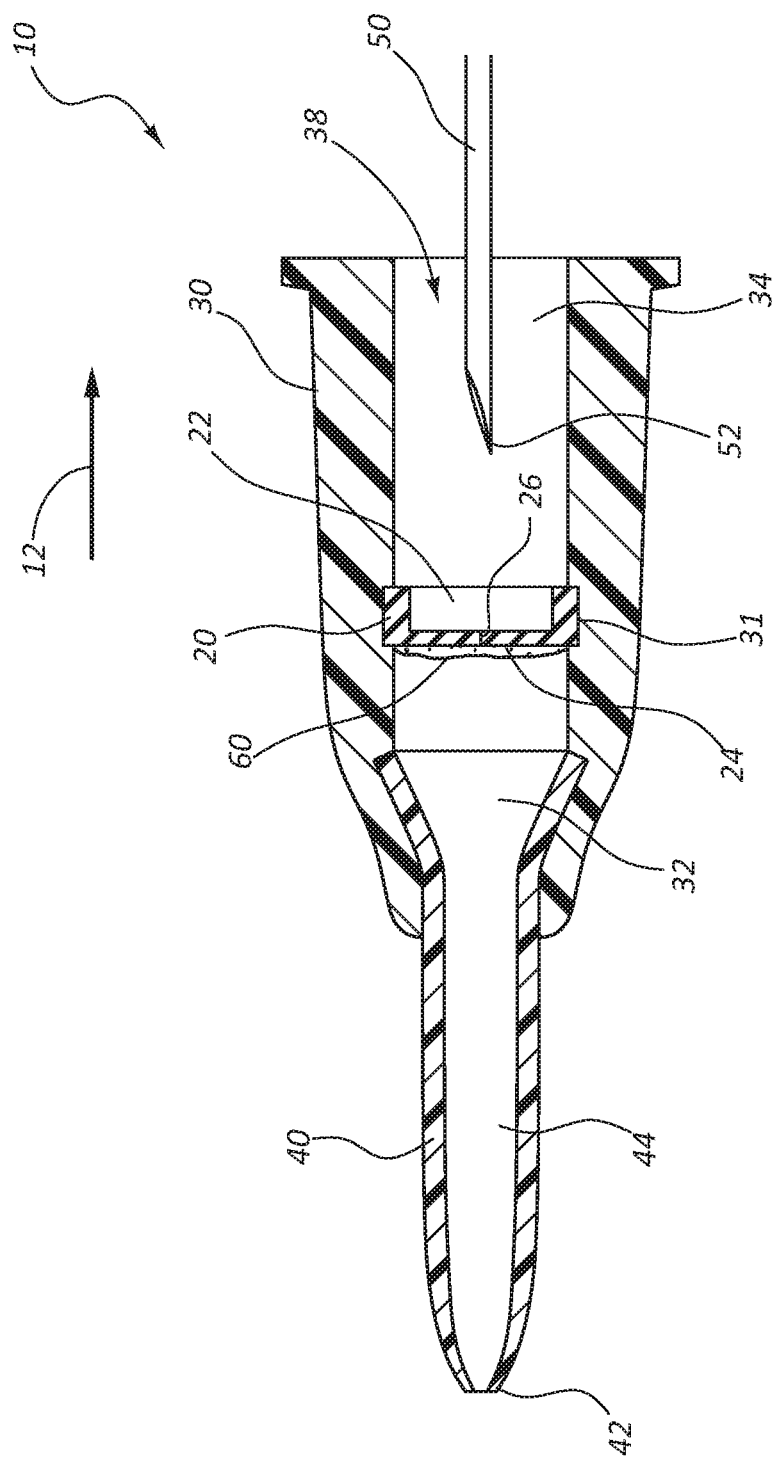
FIG. 3 is a cross-section view of a catheter assembly having a blood control septum that is coated with an antimicrobial material that was removed from the outer surface of an introducer needle by the blood control septum as the introducer needle was withdrawn from the catheter adapter in accordance with a representative embodiment of the present invention.

Upon complete withdrawal of introducer needle 50 from septum 20, slit 26 self-closes thereby providing a further physical barrier between forward and rearward chambers 32 and 34, as shown in FIG. 3. The barrier provided by excess antimicrobial lubricant 60 may further migrate to other surfaces in close proximity of the septum thus provide antimicrobial protection to the inside surfaces of the catheter beyond the septum.

Figure 4:
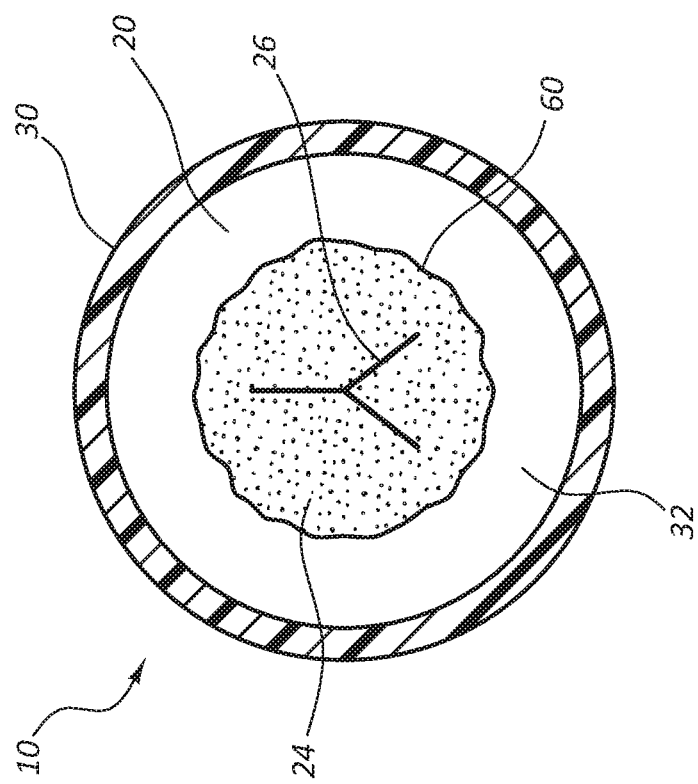
FIG. 4 is a cross-section end view of the blood control septum and deposited antimicrobial lubricant material following removal of the introducer needle in accordance with a representative embodiment of the present invention.

In some embodiments, slit 26 of blood control septum 20 comprises a tri-slit configuration, as shown in FIG. 4. Following removal of needle 50, excess antimicrobial lubricant 60 is deposited on membrane 24 thereby covering slit 26. Antimicrobial lubricant 60 prevents colonization and growth of pathogens on membrane 24.

Figure 5:
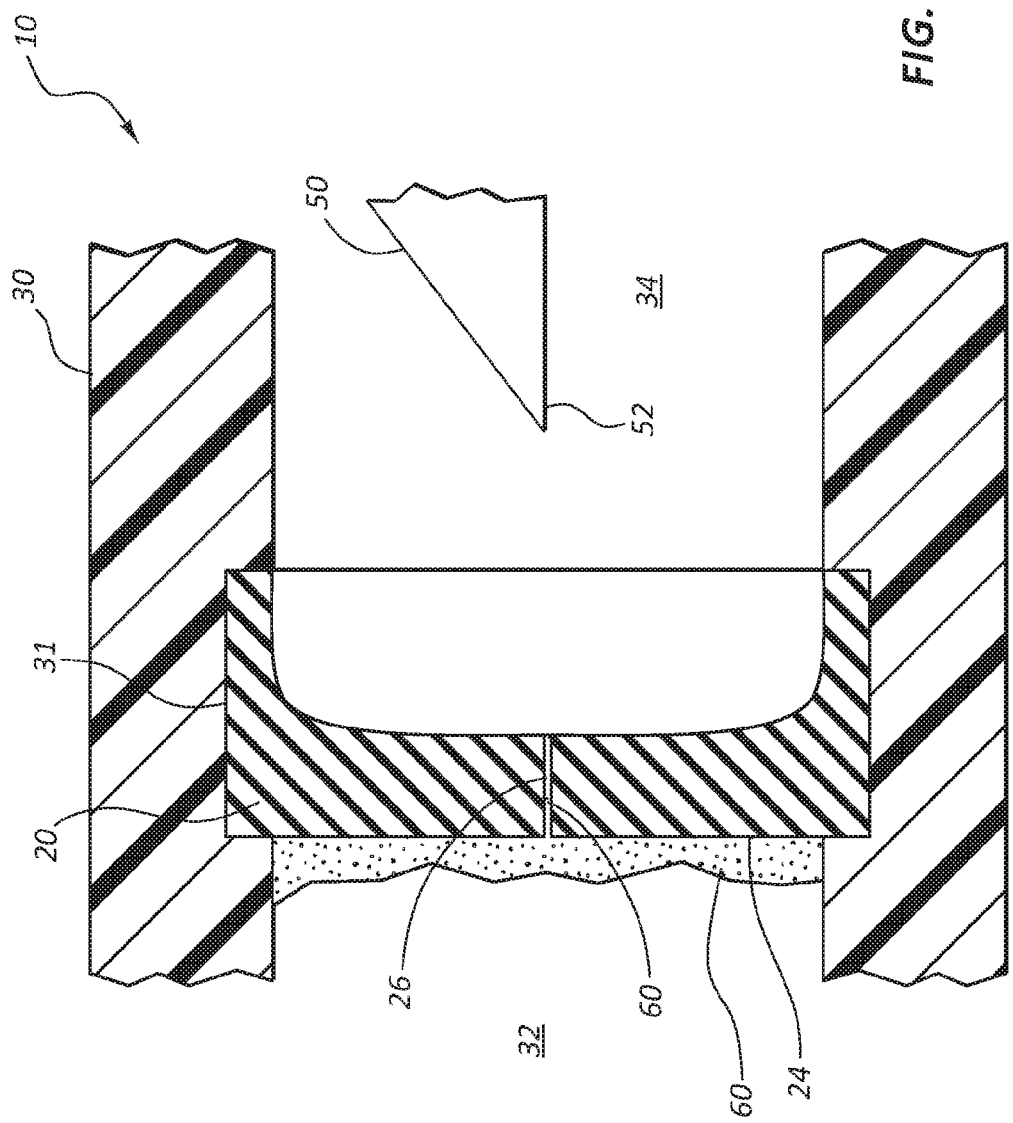
FIG. 5 is a detailed, cross-section view of the slit in the blood control septum following removal of the introducer needle, wherein residual antimicrobial lubricant material is deposited within the slit of the blood control septum in accordance with a representative embodiment of the present invention.

In some embodiments, excess antimicrobial lubricant 60 migrates into slit 26 thereby filling any gaps or openings in slit 26, as shown in FIG. 5. In this manner, excess antimicrobial lubricant 60 assists septum 20 in preventing flow of fluids between forward and rearward chambers 32 and 34.

Figure 6:
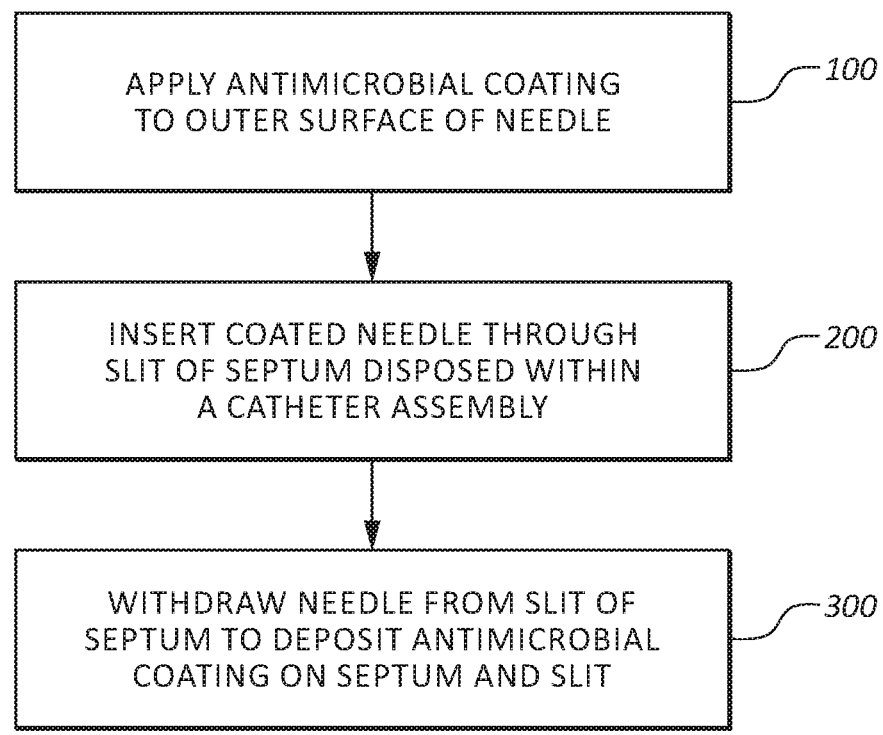
FIG. 6 is a flow chart demonstrating a method for lubricant a septum with an antimicrobial composition is accordance with a representative embodiment of the present invention.

Some implementations of the present invention further include a method for lubricant a septum of a blood control catheter with antimicrobial needle lube, as outline in FIG. 6. In some instances, a first step lubricant the septum comprises applying an antimicrobial lubricant to an outer surface of an introducer needle (at step 100). The coated needle is then inserted through the slit of a septum disposed within a catheter assembly (at step 200). In some instances, a threader is first inserted into the slit of the septum to provide an enlarged opening. In this manner, the antimicrobial lubricant is prevented from being displaced during the assembly of the device. Once positioned within the catheter assembly, the threader is removed from the slit and the device is ready for use.

The septum is coated as the needle is withdrawn from the septum and the catheter assembly device (at step 300). As the needle is withdrawn, the slit of the septum squeegees excess antimicrobial lubricant from the outer surface of the needle. This excess antimicrobial lubricant is deposited on membrane and slit portions of the septum. In some instances, excess antimicrobial lubricant is deposited within a forward chamber of the catheter assembly device to form an additional barrier between the septum and the vasculature of the patient.

Figure 8:
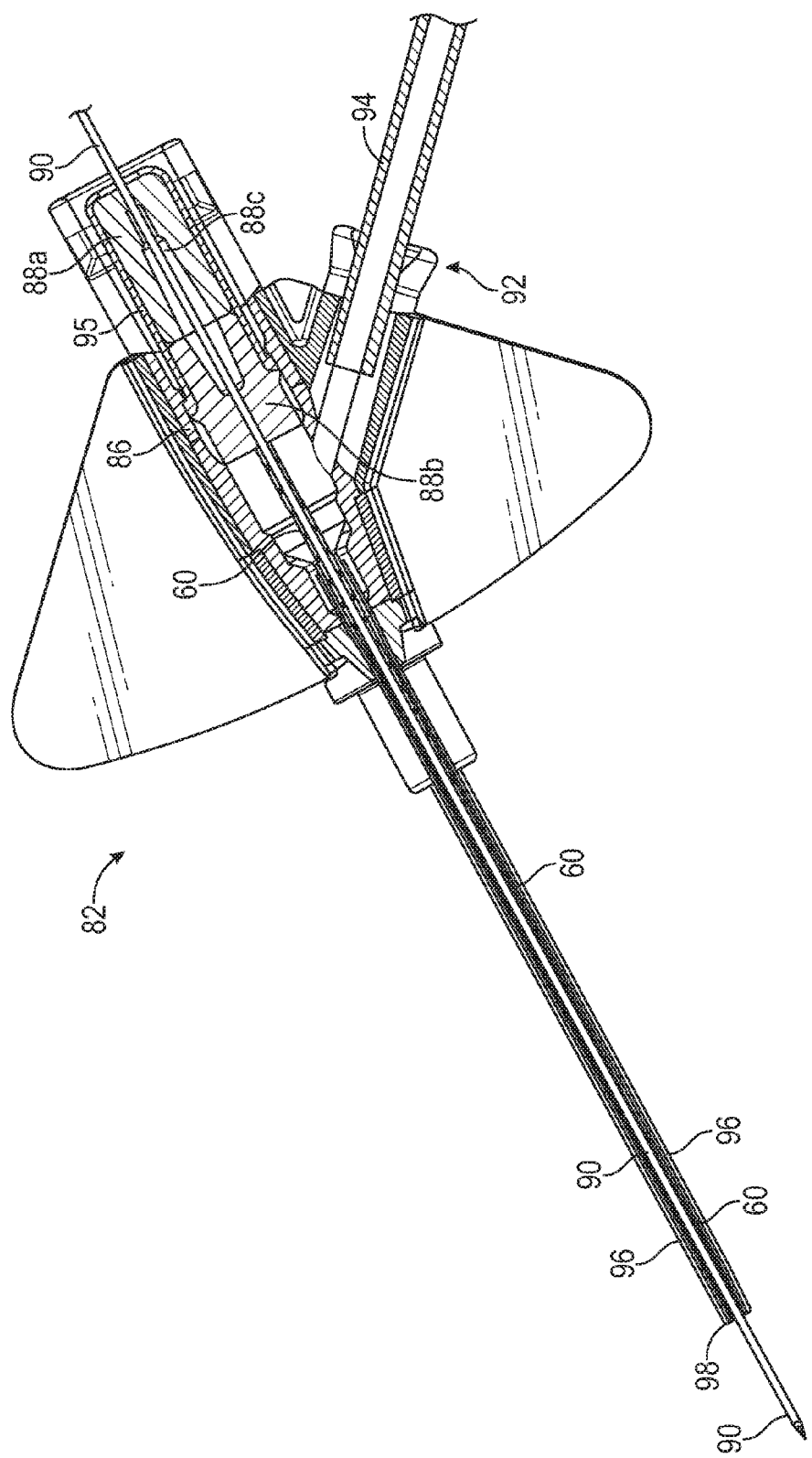
FIG. 8 is a cross-section view of another catheter assembly having a coated introducer needle positioned prior to being withdrawn from a catheter adapter in accordance with a representative embodiment of the present invention.
Figure 9:
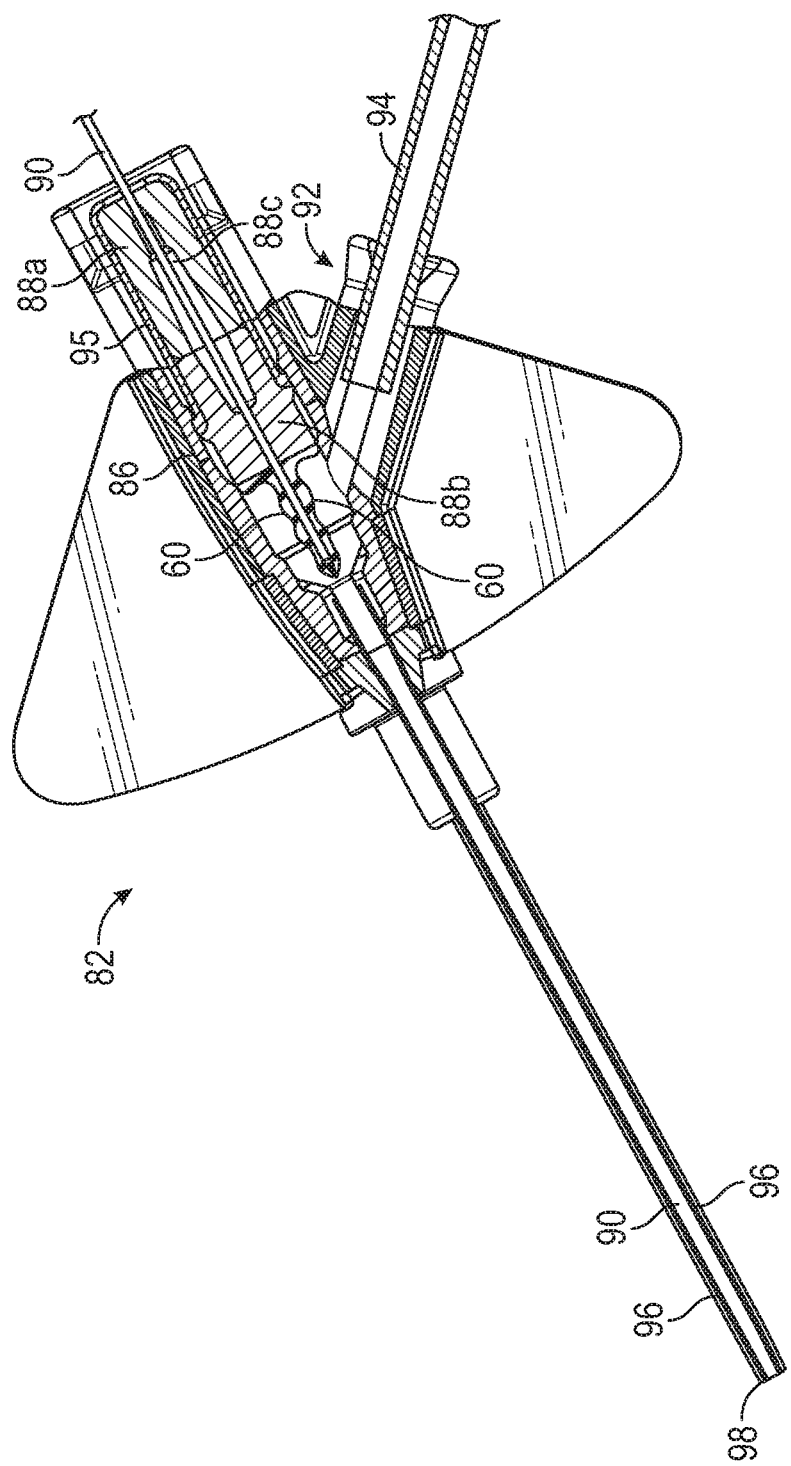
FIG. 9 is a cross-section view of the catheter assembly of FIG. 8 having the coated introducer needle partially withdrawn from the catheter adapter, wherein an antimicrobial lubricant on the introducer needle has been partially removed from the introducer needle by a septum in accordance with a representative embodiment of the present invention.
Figure 10:
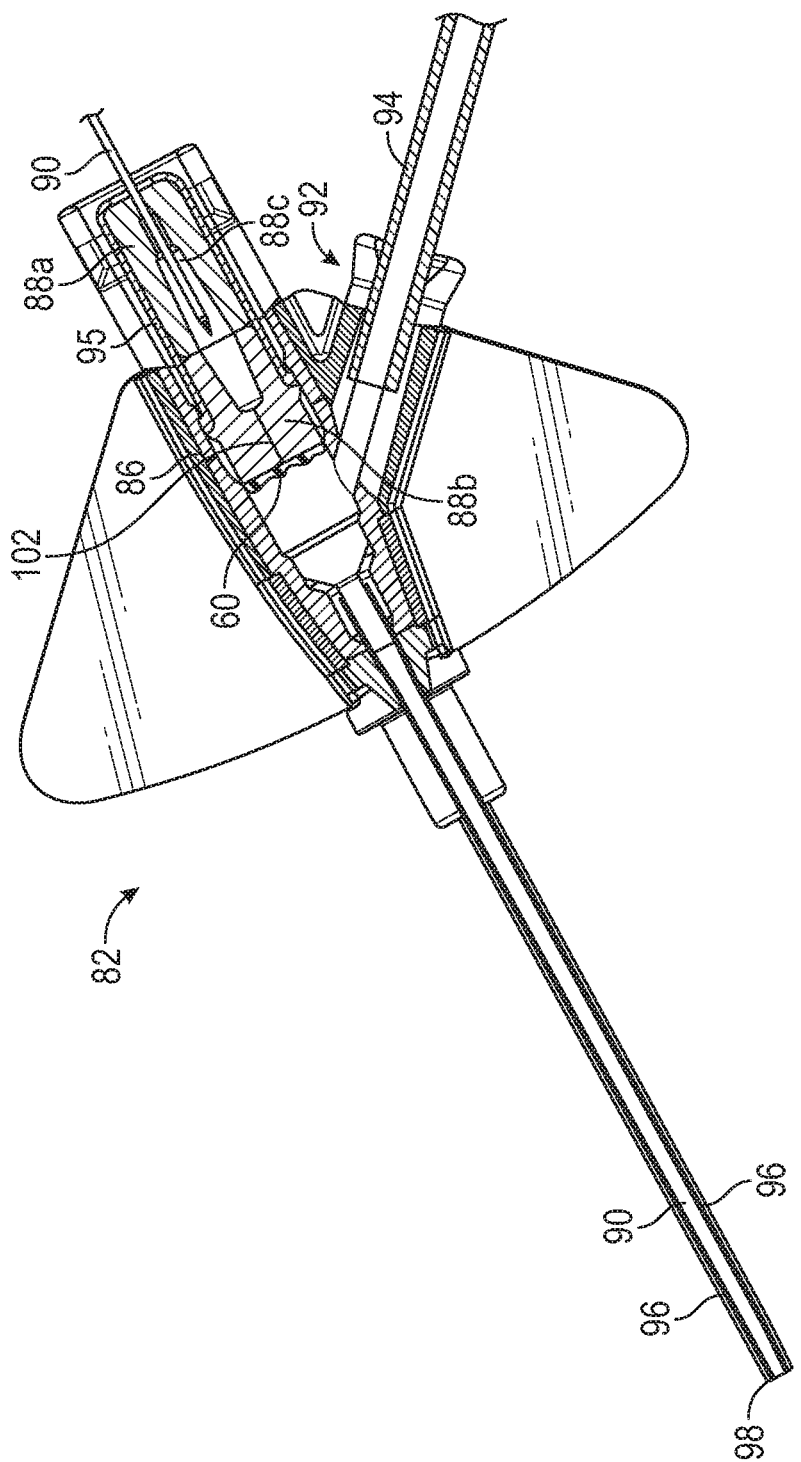
FIG. 10 is a cross-section view of the catheter assembly of FIG. 8, illustrating the septum coated with an antimicrobial material that was removed from an outer surface of the introducer needle by the septum as the introducer needle was withdrawn from the catheter adapter in accordance with a representative embodiment of the present invention.

FIGS. 8-10 illustrate another catheter assembly 82, according to some embodiments. In some embodiments, the catheter assembly 82 may correspond to the catheter assembly 10, illustrated in FIGS. 1-5. For example, in some embodiments, the septum 88 may correspond to the septum 20 of FIGS. 1-5. In some embodiments, the catheter assembly 82 may include, but is not limited to, the BD Diffusics™ Closed IV Catheter System, the BD Nexiva™ Closed IV Catheter System, the BD Intima II™ Closed IV Catheter System, or the BD Saf-T-Intima™ Closed IV Catheter System, available from Becton, Dickinson, and Company.

In some embodiments, a proximal end of the catheter adapter 86 may be sealed with the septum 88 to ensure that fluid does not exit or leak out of the proximal end of the catheter adapter 86. In some embodiments, the septum 88 may be formed from one piece. In some embodiments, the septum 88 may be formed from two portions, a proximal portion 88*a* and a distal portion 88*b*.

In some embodiments, the septum 88 may include a slit. In further detail, in some embodiments the septum 88 may be pre-slit prior to insertion of the introducer needle 90 through the septum 88 or the slit may be formed when the introducer needle 90 is inserted through the septum 88. For example, in some embodiments, one or more of the proximal portion 88*a* and the distal portion 88*b* may be pre-slit to facilitate locating an introducer needle 90 therethrough, or one or more of the proximal portion 88*a* and the distal portion 88*b* may not be pre-slit but may instead may be slit when the introducer needle 90 is inserted therethrough. In some embodiments, the septum distal portion 88*b* may provide the primary seal preventing fluid flow past septum 88 while septum proximal portion 88*a* may provide a secondary seal. Suitable materials for septum 88 may include a peroxide cured elastomer such as polyisoprene, silicone, and the like where the materials have a durometer in the range of 35-45 Shore A.

In some embodiments, the catheter adapter 86 may include a side port 92, which may include an extension tube 94 connected thereto. In some embodiments, attachment of another medical device to the proximal end of the catheter adapter may be prevented, for example, by a housing 95 which may surround at least a portion of the septum 88. Instead, any such medical device that may be connected to the catheter adapter 86 should be connected to a fluid access device (not illustrated) disposed at a proximal end of the extension tube 94. In some embodiments, the proximal end of the extension tube 94 may include a luer lock adapter or other fluid access device to allow connection of an IV fluid supply line to the extension tube 94. In some embodiments, the side port 92 may be in fluid communication with a lumen of the catheter 96 so that fluid infused through the extension tube 94 may pass into a patient once the catheter 96 is properly positioned in the patient. Conversely, in some embodiments, blood exiting a patient's vein through the catheter 96 may travel through the extension tube 94.

In some embodiments, a fluid pathway for fluid infused through the extension tube 94 and/or blood exiting the patient's vein may include at least the extension tube 94, a portion of a lumen of the catheter adapter 86 distal to the septum 88, and a lumen of the catheter 96. In some embodiments, the septum 88 may be separate from the fluid pathway. For example, the fluid pathway may not extend through the septum 88, and the septum 88 may prevent fluid in the fluid pathway from exiting the proximal end of the catheter adapter 86.

In some embodiments, the septum 88 may be disposed in the catheter adapter 86 so that at least a distal portion of septum distal portion 88b engages the inside of the catheter adapter 86. In some embodiments, an external diameter of at least the distal portion of septum distal portion 88b may be greater than an internal diameter of catheter adapter 86 at least along the portion that engages the distal portion of septum distal portion 88b. In some embodiments, the external diameter of the distal portion of septum distal portion 88b may be at least 5% larger than the internal diameter of the relevant portion of the catheter adapter 86. With this configuration, the catheter adapter 86 may exert a radial compressive force against the distal portion 88b. This compressive force may help to seal the septum distal portion 88b after the introducer needle 90 has been withdrawn from the septum 88 so that septum distal portion 88b does not take a compression set about introducer needle 90. In some embodiments, the portion of the catheter adapter 86 that engages septum distal portion 88b may be arranged such that a proximal end of septum 88 is adjacent to the open proximal end of catheter adapter 86 when the catheter adapter 86 engages the septum distal portion 88b. In some embodiments, the septum 88 may be affixed inside catheter adapter 86 using an alternate technique such as by an interference fit between the housing 95 and the catheter adapter 86, the use of an adhesive, or by ultrasonic welding.

In some embodiments, the septum 88 may define a cavity or hollow interior portion 88c formed between the septum proximal portion 88a and the septum distal portion 88b. In some embodiments, the hollow interior portion 88c may be between about 6 and about 8 millimeters in length. The hollow interior portion 88c may minimize drag on the introducer needle 90 as it is being withdrawn from the catheter assembly 82.

In some embodiments, the septum 88 may have a thickness or length of between 9 and 14 millimeters. In some embodiments, the septum 88 may have a thickness or length of between 4 and 14 millimeters.

In some embodiments, the antimicrobial lubricant 60 may include a silicone lubricant, which may have a viscosity of about 1,000,000 cp. In some embodiments, the viscosity of the antimicrobial lubricant 60 may be from 20 cp to 1,000,000 cp. In some embodiments, the antimicrobial lubricant 60 may include one or more antimicrobial agents in an amount from approximately 0.5% (w/v) to approximately 14.0% (w/v) of the antimicrobial lubricant 60.

In some embodiments, the antimicrobial lubricant 60 may be applied to at least a portion of an outer surface of the needle 90. In some embodiments, the antimicrobial lubricant 60 may be applied to only a portion of an outer surface of the needle 90. In some embodiments, the portion may be disposed distal to the septum 88 when the needle extends beyond the distal end of the catheter 96 and/or before the needle 90 is withdrawn or partially withdrawn following insertion into the vasculature of the patient. In some embodiments, the portion may extend from a distal portion of the needle 90 to a distal end of the septum 88 when the needle extends beyond the distal end of the catheter 96 and/or before the needle 90 is withdrawn or partially withdrawn following use. In some embodiments, the distal portion of the needle 90 may include a beveled tip of the needle 90.

In some embodiments, the needle 90 may be coated with the antimicrobial lubricant 60 to reduce adhesion between the needle 90 and a catheter tip 98, as well as between the needle 90 and the septum 88. Upon withdrawing the needle 90 from the catheter 96 and the septum 88, the slit 102 of the septum 88 may rub against an outer surface of the needle 90, thereby removing excess lubricant 60, as illustrated in FIG. 2-3.

In some embodiments, when the antimicrobial lubricant 60 is applied to a portion of the outer surface of the needle 90 proximate a distal end of the septum and/or distal to the distal end of the septum, this may allow the antimicrobial lubricant to be deposited on the distal end of the septum and/or the slit 102 of the septum 88 during insertion of the needle 90 through the distal opening of the catheter adapter 86 when the catheter assembly 82 is prepared for insertion into the vasculature of the patient. In some embodiments, the septum 88 may be pre-slit to include the slit 102. In some embodiments, the slit 102 may be formed in response to insertion of the introducer needle 90 through the septum 88.

Figure 11:
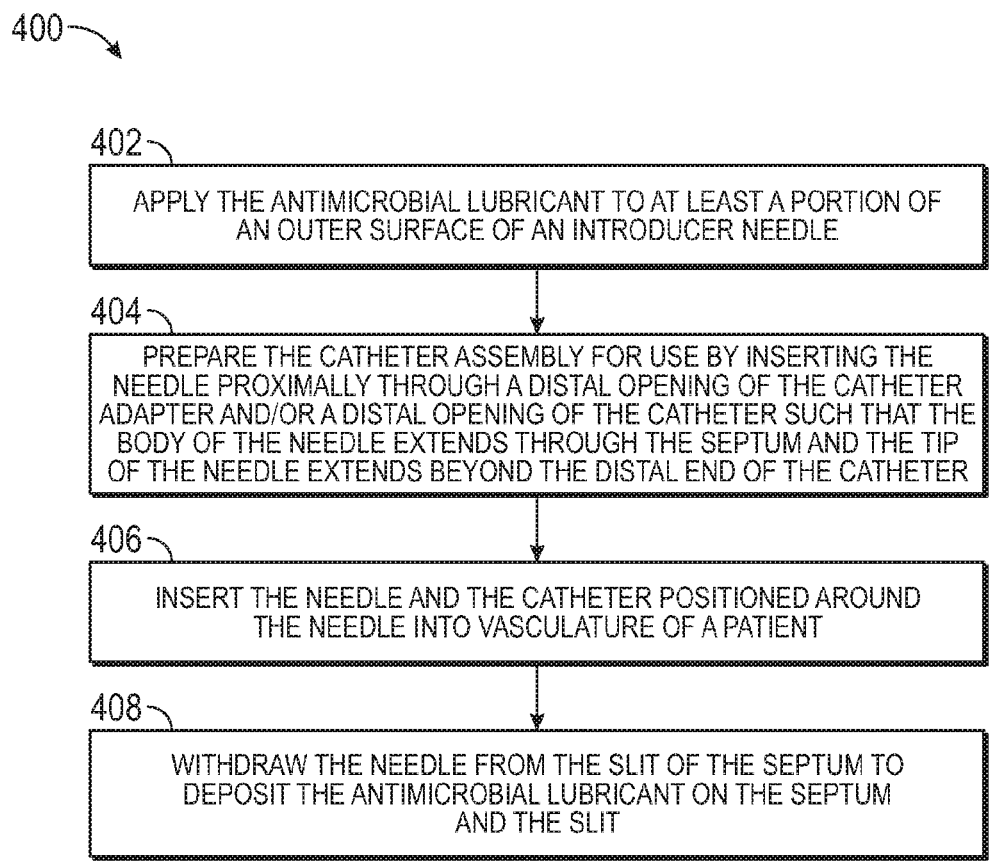
FIG. 11 is a flow chart demonstrating a method of lubricating a septum with an antimicrobial composition in accordance with a representative embodiment of the present invention.

Some implementations of the present invention may include a method 400 of lubricating a septum of a catheter assembly with an antimicrobial coating or lubricant, as illustrated in FIG. 11. In some embodiments, a first step 402 of the method 400 may include applying the antimicrobial lubricant to at least a portion of an outer surface of an introducer needle. In some embodiments, the antimicrobial lubricant may be applied to only a portion of the outer surface of a body of the needle. In some embodiments, the portion may be proximate to a distal end of the septum when the needle extends beyond the distal end of a catheter of the catheter assembly and/or before the needle is withdrawn or partially withdrawn following insertion into the vasculature of the patient. In some embodiments, the first step 402 may be followed by a second step 404.

In some embodiments, a second step 404 of the method 400 may include preparing the catheter assembly for insertion into the vasculature of the patient by inserting the needle, having the antimicrobial lubricant applied thereto, proximally through a distal opening of the catheter adapter and/or a distal opening of the catheter such that the body of the needle extends through the septum and the tip of the needle extends beyond the distal end of the catheter. In embodiments in which the antimicrobial lubricant is applied to a portion of the outer surface of the needle, the portion may be disposed distal to a distal end of the septum.

In some embodiments, when the body of the needle extends through the septum, a slit of the septum may seal around the body of the needle such that upon withdrawing the needle proximally from the slit of the septum, the slit removes a portion of the antimicrobial lubricant from the outer surface of the needle to form a deposit of the antimicrobial lubricant on the septum at a location proximate to the slit. In some embodiments, when the needle is inserted proximally through the distal opening of the catheter adapter and/or a distal opening of the catheter, a threader may not be needed to prevent the antimicrobial lubricant from being displaced during assembly of the device.

The second step 404 may not be preferred with the septum 20 illustrated in FIGS. 1-5, which may include a membrane, as insertion of the needle proximally through the septum 20 may cause the septum 20 to adopt a concave configuration. In contrast, in some embodiments, a thickness of the septum 88, illustrated in FIGS. 8-10, may allow the needle to be inserted proximally through the septum 20 without disruption of a shape of the septum 88. In some embodiments, the second step 404 may be followed by a third step 406.

In some embodiments, the third step 406 of the method 400 may include inserting the needle and the catheter positioned around the needle into vasculature of a patient. In some embodiments, the third step 406 may be followed by a fourth step 408.

In some embodiments, the fourth step 408 may include withdrawing the needle from the slit of the septum to deposit the antimicrobial lubricant on the septum and the slit. As the needle is withdrawn, the slit of the septum may squeegee excess antimicrobial lubricant from the outer surface of the needle. This excess antimicrobial lubricant may be deposited on the distal end of the septum and at least an outer surface of the slit of the septum. In some embodiments, this excess antimicrobial lubricant may be deposited within at least a distal portion of the slit.

The present invention may be embodied in other specific forms without departing from its structures, methods, or other essential characteristics as broadly described herein and claimed hereinafter. For example, the present invention may be applied to any dermally invasive device, such as needles, scalpels, trocars, endoscopes, stoma appliances, and the like. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly, comprising:
    a catheter adapter, wherein the catheter adapter comprises a proximal end, a distal end, a lumen extending therebetween, a side port connected to an extension tube, wherein a proximal end of the extension tube is configured to be connected to a fluid access device to allow fluid to flow into the catheter adapter through a fluid pathway, wherein the fluid pathway comprises the extension tube, a portion of the lumen distal to a septum, and a catheter;
    wherein a proximal end of the catheter is coupled to the distal end of the catheter adapter;
    the septum disposed in the lumen of the catheter adapter, wherein the septum prevents fluid in the fluid pathway from exiting the proximal end of the catheter adapter;
    a needle comprising a base, a tip, and a body extending therebetween, wherein the body of the needle is disposed within the lumen of the catheter adapter; and
    an antimicrobial lubricant applied to only a portion of an outer surface of the needle, wherein the portion of the outer surface extends from a distal portion of the needle to a distal end of the septum when the needle extends beyond the distal end of the catheter, wherein as the needle is withdrawn proximally through the septum, the septum removes the antimicrobial lubricant from the needle thereby depositing the antimicrobial lubricant on the distal end of the septum.

2. The catheter assembly of claim 1, wherein the antimicrobial lubricant comprises at least one of a water soluble lubricant, an insoluble lubricant, a viscous gel lubricant, and a solid lubricant.

3. The catheter assembly of claim 1, wherein the antimicrobial lubricant comprises an oil lubricant such as polydimethyl siloxane, polytrifluoropropylmethyl siloxane, or a copolymer of dimethylsiloxane and trifluoropropylmethylsiloxane.

4. The catheter assembly of claim 1, wherein the antimicrobial lubricant comprises an antimicrobial agent.

5. The catheter assembly of claim 4, wherein the antimicrobial agent is at least one of chlorhexidine dihydrochloride, chlorhexidine gluconate, chlorhexidine acetate, chlorhexidine diacetate, triclosan, chloroxylenol, dequalinium chloride, benzethonium chloride, and benzalkonium chloride.

6. The catheter assembly of claim 4, wherein the antimicrobial lubricant further comprises at least one of a fugitive solvent component, an alcohol component, and an antimicrobial agent.

7. The catheter assembly of claim 4, wherein the antimicrobial agent is a non-alcohol based antimicrobial agent.

8. The catheter assembly of claim 6, wherein the polymer component is insoluble in water.

9. The catheter assembly of claim 6, wherein the polymer component is water soluble.

10. The catheter assembly of claim 6, wherein the antimicrobial agent is present in an amount from approximately 0.001% (w/v) to approximately 10.0% (w/v).

11. The catheter assembly of claim 6, wherein the antimicrobial agent is at least one of chlorhexidine dihydrochloride, chlorhexidine gluconate, chlorhexidine acetate, chlorhexidine diacetate, triclosan, chloroxylenol, dequalinium chloride, benzethonium chloride, and benzalkonium chloride.

12. The catheter assembly of claim 6, wherein the alcohol component comprises a lower alcohol having between one and six carbon atoms.

13. The catheter assembly of claim 6, wherein the alcohol component is present within the antimicrobial lubricant in amount approximately equal to 20% (w/v).

14. The catheter assembly of claim 6, wherein the alcohol component comprises a mixture of isopropyl alcohol and ethanol, and is present within the antimicrobial lubricant in an amount from approximately 40% (w/v) to approximately 95% (w/v).

15. The catheter assembly of claim 6, wherein the fugitive solvent comprises an organic solvent that is present within the antimicrobial lubricant in an amount from approximately 20% (w/v) to approximately 95% (w/v).

16. A method for applying an antimicrobial lubricant to a septum of a catheter assembly, the method comprising:
    providing a catheter assembly, the catheter assembly comprising:
        a catheter adapter comprising a proximal end, a distal end, and a lumen extending therebetween, wherein the distal end of the catheter adapter comprises a distal opening;
        a catheter connected to the distal end of the catheter adapter, wherein the catheter comprises a distal end and a proximal end; and
        a septum disposed within the lumen;
    applying an antimicrobial lubricant to a portion of an outer surface of a needle, wherein the needle comprises a base, tip, and a body extending therebetween;

preparing the catheter assembly for insertion into vasculature of the patient by inserting the needle proximally through the distal opening of the catheter adapter such that the body of the needle extends through the septum, the tip of the needle extends beyond the distal end of the catheter, and the portion is disposed distal to a distal end of the septum, wherein when the body of the needle extends through the septum, a slit of the septum seals around the body of the needle such that upon withdrawing the needle proximally from the slit of the septum, the slit removes a portion of the antimicrobial lubricant from the portion of the outer surface of the needle to form a deposit of the antimicrobial lubricant on the septum at a location proximate to the slit.

17. The method of claim 16, wherein a fluid pathway extending through the catheter adapter does not extend through the septum.

18. The method of claim 16, wherein the septum is configured to prevent fluid from exiting a proximal end of the catheter adapter, wherein the catheter adapter further comprises a side port connected to an extension tube, wherein a proximal end of the extension tube is configured to be connected to a fluid access device to allow fluid to flow into the catheter adapter through a fluid pathway that does not extend through the septum, wherein the fluid pathway comprises the extension tube, a portion of the lumen distal to the septum, and the catheter.

19. A method of depositing an antimicrobial agent on a septum of a catheter adapter after insertion of a catheter into vasculature of a patient, the method comprising:

applying an antimicrobial lubricant to an outer surface of a needle, wherein the needle comprises a base, a tip, and a body extending therebetween;

preparing a catheter assembly for insertion into vasculature of a patient, wherein the catheter assembly comprises a catheter adapter having a lumen extending therethrough, a catheter connected to the catheter adapter, and septum disposed in the lumen, wherein preparing the catheter assembly for insertion into the vasculature comprises inserting the needle proximally through the distal opening of the catheter adapter such that the lubricant is not removed from the needle during insertion through the distal opening;

inserting the needle and the catheter positioned around the needle into the vasculature of the patient; and withdrawing the needle from the catheter such that, as the needle passes through a slit in the septum, the slit removes the antimicrobial lubricant from the needle thereby forming a deposit of the antimicrobial lubricant around the slit of the septum.

20. The method of claim 19, wherein the catheter adapter comprises a side port connected to an extension tube, wherein a proximal end of the extension tube is configured to be connected to a fluid access device to allow fluid to flow into the catheter adapter through a fluid pathway separate from the septum, wherein the fluid pathway comprises the extension tube, a portion of the lumen distal to the septum, and the catheter.

* * * * *